US00PP17389P3

(12) United States Plant Patent
Lemon

(10) Patent No.: US PP17,389 P3
(45) Date of Patent: Jan. 30, 2007

(54) ***GERANIUM* PLANT NAMED 'MAIDEN DEEP LAVENDER'**

(50) Latin Name: *Pelargonium×domesticum*
Varietal Denomination: Maiden Deep Lavender

(75) Inventor: David G. Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 11/210,253

(22) Filed: Aug. 23, 2005

(65) Prior Publication Data

US 2006/0059596 P1 Mar. 16, 2006

Related U.S. Application Data

(60) Provisional application No. 60/603,724, filed on Aug. 23, 2004.

(51) Int. Cl.
*A01H 5/00* (2006.01)

(52) U.S. Cl. ..... Plt./331

(58) Field of Classification Search ..... Plt./331
See application file for complete search history.

*Primary Examiner*—Kent Bell

*Assistant Examiner*—June Hwu

(74) *Attorney, Agent, or Firm*—The Webb Law Firm

(57) ABSTRACT

'Maiden Deep Lavender' is a new variety of Regal *Geranium* having compact growth and variegated lavender colored flowers with a distinctive eye.

1 Drawing Sheet

Botanical classification: *Pelargonium×domesticum.*
Varietal denomination: 'Maiden Deep Lavender'.

BACKGROUND OF THE INVENTION

The present invention comprises a new and distinct cultivar of *Pelargonium×domesticum* known by the varietal name 'Maiden Deep Lavender'. The new variety was discovered in Lompoc, Calif. The new variety is a result of cross-breeding the unpatented 'Austria' variety, (female parent) and 'Barroness' (male parent) (U.S. Plant Pat. No. 8,908). The purpose of the breeding program was to introduce a high quality compact regal *geranium*. The new variety exhibits similar flower size and the early flowering of both parents with different flower color than either parent. 'Maiden Deep Lavender' is similar to 'Maiden Lilac' (U.S. Plant Pat. No. 10,420) but exhibits heavier blotching on petals and a more controlled compact habit. The new variety was first asexually reproduced by cuttings in Connellsville, Pa. The new variety has been trial and field tested and has been found to retain its distinctive characteristics and remain true to type through successive propagations.

The new variety was grown in a glass greenhouse in a 4 inch pot in Connellsville, Pa. using full light, 60° F. night temperature and 68° F. day temperature and grown in a soilless media with constant fertilizer at 150–200 ppm nitrogen and potassium. The new variety has a response time of twelve weeks from a rooted cutting to flowering in a 6 inch container.

The following traits have been repeatedly observed and are determined to be unique characteristics of 'Maiden Deep Lavender'. Characteristics that distinguish 'Maiden Deep Lavender' as a new and distinct cultivar from others known to the breeder include:

1) Very early flowering; and

2) Very free flowering.

DESCRIPTION OF THE DRAWING

The accompanying photographic drawing illustrates the new variety, with the color being as nearly true as is possible with color illustrations of this type.

DESCRIPTION OF THE PLANT

Figure 1:
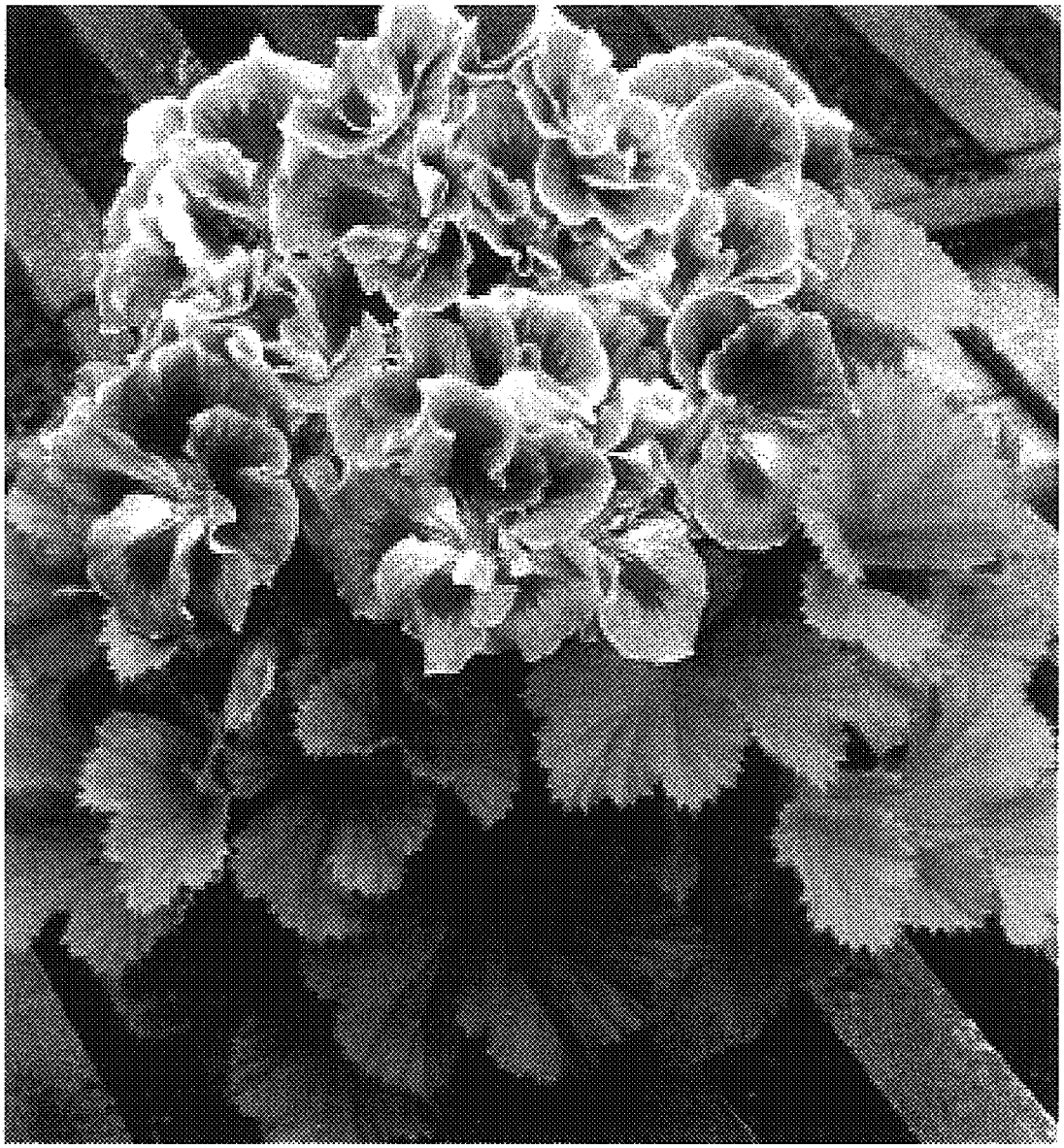

The following detailed description sets forth the characteristics of the new cultivar. The data which defines these characteristics were collected by asexual reproductions carried out in Connellsville, Pa. The color readings were taken indoors under 65 to 85 footcandles of cool White fluorescent light. The new variety was fifteen weeks from a rooted cutting when described. Color references are primarily to the 1966 R.H.S. Colour Chart of The Royal Horticultural Society of London.

PLANT

Market class: Regal.
Rooting time: Visible roots can be seen on the outside of a plug in 25 days under optimal conditions.
Form: Medium mound habit.
Height from media surface to top of foliage: 19 cm in a 6 inch pot.
Strength (need for artificial support): No artificial support is needed.
Branching habit: Free basal branching.
Plant spread: 17–20 cm.
Stem:
- *Color.*—144A.
- *Internode length.*—1.5 to 3 cm.
- *Surface texture.*—Smooth with fine hairs present.

Foliage:
- *Arrangement.*—Alternate.
- *Stipules.*—Number: Two at each node. Length: 1.0 cm. Width: 0.8 cm. Color: 144A.

*Zone.*—None present.
*Size of leaf.*—Length: 5.0 to 6.5 cm at longest point. Width: 5.5 to 7.5 cm at widest point.
*Shape of leaf* (*generally*).—Reniform with a truncate base and a reniform apex.
*Texture.*—Leathery.
*Margin type.*—Serrated; lobed.
*Pubescence.*—Slight.
*Color.*—Upper surface: 137B. Lower surface: 144A.
*Petiole.*—Length: 3 to 4.5 cm. Color: 144A.
*Veins.*—Venation type: Palmate. Color: 145A.

INFLORESCENCE

Bud: Stage of development when bud characteristics determined: Just prior to sepals parting at the tips.
*Shape of cluster.*—Elliptical.
*Diameter of cluster.*—3.8 to 4.2 cm across; 2.0 to 2.3 cm deep.
*Number of buds per cluster.*—5 to 8.
*Shape of individual bud.*—Elliptical or oval.
*Length of individual bud.*—1.2 to 1.3 cm.
*Width of individual bud.*—0.7 cm.
*Sepals.*—Number: Six. Length: 1.3 to 1.4 cm. Width: 0.6 cm. Shape: Lanceolate. Color: 144A.
Blooming habit: Continuous, free to flowering, large flowers forming full color heads, early flowering.
Umbel diameter: 7.5 to 9.5 cm.
Borne: Umbel, flowers on pedicel, pedicel on peduncle.
Inflorescence position: 4 to 6 cm above foliage.
Number of inflorescences per lateral branch: 1 to 3.
Florets:
*Average number per umbel.*—5 to 8.
*Form.*—Cupped at base. As the flowers mature, the florets gradually become more open/flat.
*Diameter.*—5.5 to 6.5 cm.
*Depth.*—1.5 to 2 cm.
Petals:
*Color.*—All petals have a dark eye. The eye is more pronounced and much larger on upper three petals than on lower petals.
*Upper surface.*—The outer edge color is 78A moving to 74A at outer edge of the dark eye. The eye is colored 187B. Near the lower quarter of the petal, the eye ends and the color sharply changes to 155C, with pronounced veining of 187A, 72A and 71A. Lower petals are same color as upper, but with a smaller eye.
*Lower surface.*—The outer edge color is 78A moving to 74A at outer edge of the eye. Eye color is 187C. At the lower quarter of the petal, the eye ends and the petal color becomes 155C, with dark veining of 187B and 71A.
*Shape.*—Inverted teardrop.
*Length.*—3.5 to 4 cm.
*Width.*—2.5 to 4 cm.
*Margin.*—Entire.
*Number per floret.*—5 to 6.
*Texture.*—Velvety, smooth, highly reflective.
Petaloids: None.
Pedicel:
*Length.*—2.3 to 2.6 cm.
*Color.*—144B.
*Surface texture.*—Smooth with fine hairs present.
Peduncle:
*Length.*—5 to 6 cm.
*Color.*—144A.
*Surface texture.*—Smooth with fine hairs present.
Fragrance: None noted.
Disease/pest resistance: No unusual susceptibility to disease or pests has been noted to date.
Lastingness: Individual umbels last 14 to 21 days.

REPRODUCTIVE ORGANS

Stamens:
*Number* (*per flower*).—5 to 7.
*Filament.*—Length: 13 to 15 mm. Color: 155D.
*Anthers.*—Length: 2 to 3 mm. Color: 77A.
*Pollen color.*—28A.
Pistils:
*Number.*—1.
*Length.*—16 to 18 mm.
*Style.*—Length: 10 to 12 mm. Color: 71C.
*Stigma.*—Shape: Style splits and radiates into 5 parts. Color: 71A.
*Ovaries.*—Completeness: Superior. Pubescence: Present. Length: 6 to 8 mm. Width: 3 mm. Color: 138C.

I claim:

1. A new and distinct variety of *Geranium* plant named 'Maiden Deep Lavender' as is herein described and illustrated.

* * * * *